United States Patent [19]

Sandage et al.

[11] Patent Number: 5,801,160
[45] Date of Patent: Sep. 1, 1998

[54] METHOD OF PROTECTING BRAIN TISSUE FROM CEREBRAL INFARCTION SUBSEQUENT TO ISCHEMIA

[75] Inventors: Bobby Winston Sandage, Acton; Marc Fisher, Shrewsbury; Kenneth Walter Locke, Littleton, all of Mass.

[73] Assignee: Interneuron Pharmaceuticals, Inc., Lexington, Mass.

[21] Appl. No.: 820,244

[22] Filed: Mar. 18, 1997

Related U.S. Application Data

[63] Continuation of Ser. No. 399,262, Mar. 6, 1995, abandoned.

[51] Int. Cl.$^6$ .................................................. A61K 31/70
[52] U.S. Cl. ................................................................ 514/49
[58] Field of Search .................................................. 514/49

[56] References Cited

U.S. PATENT DOCUMENTS

| 4,386,077 | 5/1983 | Borgo | 424/180 |
| 4,386,078 | 5/1983 | Horrocks et al. | 424/180 |

FOREIGN PATENT DOCUMENTS

| 0075382 | 3/1970 | Japan . |
| 0074595 | 9/1973 | Japan . |
| 0075999 | 5/1982 | Japan . |
| 0108098 | 7/1982 | Japan . |
| 0108099 | 7/1982 | Japan . |

OTHER PUBLICATIONS

The Ancrod Stoke Study Investigators, Ancrod for the Treatment of Acute Ischemic Brain Infarction *Stroke*. 1994, 25:1755–1759.
Bell et al., A Novel Treatment for Ischemic Intracranial Hypertension in Cats. *Stroke*. 1991 22:80–83.
del Zoppo et al., Thrombolytic Intervention in Acute Thrombotic and Embolic Stroke. *Seminars in Neurology*. 1991 11/4;368–384.
Diener et al., The Effect of Lubelezole in the Acute Treatment of Ischemic Stroke: Results of a Phase 2 Trail *Stroke*. 1995 26:30.
Hacke et al., The Efficacy of IV–tPA in Acute Ischemic Stroke; First Results of the ECASS Trail *Stroke*. 1995 26:167.
Kaste et al., A Randomized, Double–blind, Placebo–Controlled Trail of Nimodipine in Acute Ischemic Hemispheric Stroke. *Stroke*. 1994 25:1348–1353.
Kinouchi et al., Attenuation of focal cerebral ischemic injury in transgenic mice overexpressing CuZn superoxide dismutase. *Proc. Natl. Acad. Sci. USA*. 1991 88:11158–11162.
Minematsu et al., Diffusion weighted magnetic resonance imaging: Rapid and quantitative detection of focal brain ischemia. *Neurology* 1992 42:235–240.
Olney et al., NMDA Antagonist Neurotoxicity: Mechanism and Prevention. *Science* 1991 254:1515–1518.
Ulus et al., Choline increases acetylcholine release and protects against the stimulation–induced decrease in phosphatide levels within membranes of rat corpus striatum. *Brain Research* 1989 484:217–227.

Zea Longa et al., Reversible Middle Cerebral Artery Occulsion Without Craniectomy in Rats. *Stroke* 1989 20:84–91.
Windholtz et al. (eds.), *The Merck Index*, 19$^{th}$ Ed., Merck & Co., Inc. Rahway, NJ, 1983, entry 2290 at p. 329.
Makishima et al., "Treatment of Sensory–Neural Deafness and Tinnitus with a Nucleic Acid Derivative," *Arzeneimittel Forsch. Dtsh.*, 21,(9),1343–1349 (1971).
Nilsson, "CDP–Choline–A Short Review," *Clin. Pharmacol. Drug Epidemiol.* 2,273–277 (1979).
Phuong et al., "Nouvell Méthode de Préparation de al Cytidine Diphosphate Choline (CDP Choline)", *Bull. Soc. Chim. Fr. Pt. II.*, 1979(9–10), 518–519.
Gannaro et al. (eds.), *Remmington's Pharmaceutical Sciences*, 18$^{th}$ ed., Mack Publishing Co., Easton, PA, 1990, see pp. 867, 1014 and 1026 as marked.
Sanchez et al., "CDP–Choline:Physico–Chemical Characteristics," *Arzneimittel Forschung–Drug Research*, 33(II), 1011–1012(1983).
Algate et al., "Study of the Effects of Oral Administration of CDP–Choline on EEG Changes and Lethality Induced by Epidural Compressions in the Anaethestized Cat." *Arzneimittel Forschung–Drug Research*, 33(II), 1013–1016(1983).
Agut et al.(I), "Dissimilar Effects in Acute Toxicity Studies of CDP–Choline and Choline," *Arzneimittel Forschung–Drug Research*, 33(II), 1016–1018(1983).
Braso et al., "Action of CDP–Choline by Intraduodenal Route on Rat Cardiorespitory System," *Arzneimittel Forschung–Drug Research*, 33(II), 1043–1045 (1983).
Agut et al.(II, "Bioavailability of Methyl–$^{14}$C CDP–Choline and Choline by Oral Route." *Arzneimittel Forschung–Drug Research*, 33(II), 1045–1047(1983).
Agut et al. (III), "Radioactivity Incorporation into Different Cerebral Phospholipids after Oral Administration of $^{14}$C Methyl CDP–Choline," *Arzneimittel Forschung–Drug Research*, 33(II), 1048–1050 (1983).
Aguilar et al., "Cerebral Subcellular Distribution of CDP–Choline and/or its Metabolites after Oral Administration of Methyl–$^{14}$C CDP–Choline," *Arzneimitel Forschung–Drug Research*, 33(II), 1051–1053(1983).
Romero et al.(I), "Low–Resolution Autoradiography in Rat Brain after Administering Labeled CDP–Choline Administration," *Arzeimittel Forschung–Drug Research*, 33(II), 1054–1056(1983).
Romero et al.(II), "High–Resolution Autoradiography in Mouse Brain 24 h after Radiolabelled CDP–Choline Administration," *Arzeimittel Forschung–Drug Research*, 33(II), 1056–1058(1983).
Romero et al.(III), "High–Resolution Autoradiography in Mouse Brain and Cerebellum 10 days after Radiolabelled CDP–Choline Administration," *Arzneimittel Forschung–Drug Research*, 33(II), 1058–1060(1983).

(List continued on next page.)

*Primary Examiner*—Marianne M. Cintins
*Assistant Examiner*—M. Moezie
*Attorney, Agent, or Firm*—Lowe, Price, LeBlanc & Becker

[57] ABSTRACT

Methods and pharmaceutical compositions for reducing the extent of infarction, particularly cerebral infarction subsequent to cerebral ischemia.

11 Claims, 1 Drawing Sheet

OTHER PUBLICATIONS

Dinsdale et al. (I), "CDP–Choline: Repeated Oral Dose Tolerance Studies in Adult Healthy Volunteers," *Arzneimittel Forschung–Drug Research*, 33(II), 1061–1065(1983).

Arrannz et al. "Treatment of Chronic Dyskinesia with CDP–Choline," *Arzneimittel Forschung–Drug Research*, 33(II), 1071–1073(1983).

Tornos et al. (I), "Effect of Oral CDP–Choline on Experimental Withdrawal Syndrome," *Arzneimittel Forschung–Drug Research*, 33(II), 1018–1021 (1983).

Tornos et al. (II), "Pharmacological Study of CDP–Choline," *Arzneimittel Forschung–Drug Research*, 33(II), 1022–1024(1983).

Grau et al.(1), "Study on the Protection of CDP–Choline against Nicotine Intoxification," *Arneimittel Forschung–Drug Research*, 33(II), 1025–1026(1983).

Tornos et al. (III), "Pharmacological Study of Oral CDP–Choline," *Arzneimittel Forschung–Drug Research*, 33(II), 1026–1029(1983).

Agut et al. (IV), "Effect of Oral CDP–Choline on Acrylamide–induced Lesion." *Arzeimittel Forschung–Drug Research*, 33(II), 1029–1033(1983).

Grau et al. (II), "CDP–Choline: Acute Toxicity Study," *Arzneimittel Forschung–Drug Research*, 33(II), 1033–1034(1983).

Romero et al.(IV), "Study of Subacute Toxicity of CDP–Choline after 30 days of Oral Administration to Rates," *Arzneimittel Forschung–Drug Research*, 33(II), 1035–1038(1983).

Romero et al. (V), "CDP–Choline: 6–Month Study on Toxicity in Dogs," *Arzneimittel Forschung–Drug Research*, 33(II), 1038–1042(1983).

Dinsdale et al. (II), "Pharmacokinetics of $^{14}$C CDP–Choline," *Arzneimittel Forschung–Drug Research*, 33(II), 1066–1070(1983).

Fernandez, "Efficacy and Safety of Oral CDP–Choline," *Arzneimittel Forschung–Drug Research*, 33(II), 1073–1080(1983).

Table of Contents, Key Word Index and Prefacea[a] (J.A. Ortiz) Introducing the Series of Papers on Cytidine Diphosphate Choline, *Arzneimittel Forschung–Drug Research*, 33(II), 1009–1010a[a] (1983) and preceding pages.

Cohen et al., "Decreased Brain Choline Uptake in Older Adults–An In Vivo Proton Magnetic Resonance Spectroscopy Study," *J. Am. Medical Association*, 274(11),902–907 (1995).

Fukunaga et al. (I), "Hypotensive Effects of Adenosine and Adenosine Triphosphate Compared with Sodium Nitroprusside," *Anesthesia and Analgesia*, 61(3), 273–278 (1982).

Trovarelli, G. et al., "Effect of Cytidine on the Modification of Phospholipid Metabolism Induced by Ischemia", *Neurochemical Research*, vol. 12, No. 3, 1987, pp. 227–235.

Trovarelli, G. et al., "The Influence of Cytidine on the Endogenous Pool of CDP–Choline, CDP–Ethanolamine, and CMP of the Rat Brain", *Neurochemical Research*, vol. 9, No. 1, 1984, pp. 73–79.

Trovarelli, G. et al., "The Transport of Cytidine into Rat Brain In Vivo, and its Conversion into Cytidine Metabolites", *Neurochemical Research*, vol. 7, No. 10, 1982, pp. 1199–1207.

De Medio, G.E. et al., "The Effect of Cytidine–Diphosphate Choline (CDP–Choline) on Brain Lipid Changes During Aging", *Journal of Neuroscience Research*, 11:49–58 (1984).

Petkov, V.D. et al., "Effects of Cytidine Diphosphate Choline on Rats with Memory Deficits", *Institute of Phisiology, Bulgarian Academy of Science, Sofia, Bulgaria*, Arzneim.–Forsch/Drug Res. 43(II), Nr. 8 (1993).

Kottler, P.D. et al., "RNA Metabolism in the Rat Brain During Learning Following Intravenous and Intraventricular Injections of 3H–Cytidine", *Physiology and Behavior*, vol. 8, pp. 291–297 (1992).

Wurtman, R.J. et al., "The 'Autocannibalism' of Choline–Containing Membrane Phospholipids in the Pathogenesis of Alzheimer's Disease", *Dept. of Applied Biological Sciences, Cambridge, MA, USA and Pharmacology Department, Université, Suisse*, 1990.

Buyukuysal, R.L. et al., "4–Aminopyridine Increases Acetylcholine Release Without Diminishing Membrane Phosphatidylcholine", *Journal of Neurochemistry*, vol. 54, No. 4, 1990, pp. 1302–1309.

Savci, V. et al., "Effect of Cytidine on Membrane Phospholipid Synthesis in Rat Striatal Slices", *Journal of Neurochemistry*, vol. 64, No. 1, 1995, pp. 378–384.

"A Randomized, Double–blind, Placebo–Controlld Trial of Nimodipine in Acute Ischemic Hemispheric Stroke", Kaste, Markku, et al., *Stroke*, vol. 25, No. 7, July 1994, pp. 1348–1353.

"The Dissociation of Cerebral Blood Flow, Metabolism, and Function in the Early Stages of Developing Cerebral Infarction", Kogure, K., et al., *Annals of Neurology*, vol. 8, No. 3, Sep. 1980, pp. 278–290.

"Systemic and Cerebral Hemodynamic Responses to the Noncompetitive N–Methyl–D–Aspartate (NMDA) Antagonist CNS 1102", Grosset, D.G., et al., *Journal of Cardiovascular Pharmacology*, vol. 25, No. 5, 1995, pp. 705–709.

"Effects of NMDA and Calcium Channel Antagonists on Regional Cerebral Blood Flow", Lo, Eng H., *Neuroscience Letters*, 131, (1991), pp. 17–20.

"Glutamate Receptor Antagonists in Experimental Focal Cerebral Ischaemia", McCulloch, J., et al., *Acta Neurochir*, (1993) [Suppl] 57:73–79.

"Dexamethasone Prevents Cerebral Infarction Without Affecting Cerebral Blood Flow in Neonatal Rats", Tuor, U.I., et al., *Stroke*, vol. 24, No. 3, Mar. 1993, pp. 452–457.

"Can Raising Cerebral Blood Flow Improve Outcome After Acute Cerebral Infarction", Grotta, James, *Stroke*, Vo. 18, No. 1, Jan.–Feb. 1987, pp. 264–267.

"Mechanisms of Cerebral Protection by Pentobarbital and Nizofenone Correlated with the Course of Local Cerebral Blood Flow Changes", Ochiai, Chikayuki, et al., *Stroke*, Vo. 13, No. 6, Nov.–Dec. 1982, pp. 788–796.

"Finding New Drugs to Treat Stroke", Barinaga, *Science*, vol. 272, May 3, 1996, pp. 664–666.

"Lack of Evolution of the Cerebral Blood Flow During Clinical Recovery of a Stroke", Demeurisse, G., et al., *Stroke*, vol. 14, No. 1, Jan.–Feb. 1983, pp. 77–81.

Altman R. et al. *British Medical Journal* (1994) 308:81–106.

Guiraud–Chaumeil B. et al. *Revue Neurologie* (1982) 138/5:, 367–385 (In French).

Lowenthal A. et al. *Acta Neurologica Belgique* (1994) 94:24–34.

The Canadian Cooperative Study Group, *New England Journal of Medicine* (1978) 299:53–59.

The ESPS Group, "The European Stroke Prevention Study." (1990) *Stroke* 21:1122–1130.

Minematsu, K. et al. *Cerebrovasc. Dis.* (1993) 3:99–104.

Schabitz, W. et al. *Journal of the Neurological Sciences* (1996) 138:21–25.

D'Orlando, K.J. et al. *Neurological Research* (1995) 17:281–284.

Abstract: "Effects of Citicoline on infarct volume, mortality and behavioral outcome after temporary local ischemia" by: Johannes Weber et al., dated: Jan. 9, 1995, European Stroke Conference, Bordeaux, France Jun. 1–3, 1995.

HCAPLUS Abstract, AN 1988:143195, Kakihana, M. et al. (1988).

"The Merck Index" (11th Ed.) Budavari et al., Merck & Co. Inc., Rahway, N.J., (1989) pp. 361–362.

Medline Abstract 93230870, Feb. 1993, Rossi, M. et al.

Embase Abstract 81026199, 1980, Girotto, T. et al.

Medline Abstract 80188636, 1980, Canino, V. et al.

METHOD OF PROTECTING BRAIN TISSUE FROM CEREBRAL INFARCTION SUBSEQUENT TO ISCHEMIA

This application is a continuation of application Ser. No. 08/399,262 filed Mar. 6, 1995, now abandoned.

FIELD OF THE INVENTION

The present invention relates to methods and pharmaceutical compositions for reducing the extent of infarction, particularly cerebral infarction subsequent to ischemia. More particularly, the present invention relates to the use of citicoline to reduce cerebral infarct volume.

BACKGROUND OF THE INVENTION

The brain, more than any other organ in the body, depends, for its survival and proper functioning, on a relatively constant supply of oxygenated blood. While comprising only 2% of the body's weight, the brain receives 15% of the heart's output of blood and consumes 20% of the oxygen used by the body. In addition, a constant supply of blood is required to provide the brain with glucose, the major energy substrate used by the brain to produce high-energy phosphates such as ATP.

Ischemia may be defined as the loss of blood flow to a tissue. Cerebral ischemia is the interruption or reduction of the blood flow in the arteries feeding the brain, usually as a result of a blood clot (thrombus) or other matter (embolus) occluding the artery. Loss of blood flow to a particular vascular region is known as focal ischemia; loss of blood flow to the entire brain, global ischemia.

Once deprived of blood—and, hence, oxygen and glucose—brain tissue may undergo ischemic necrosis or infarction. The metabolic events thought to underlie such cell degeneration and death include: energy failure through ATP depletion, cellular acidosis, glutamate release, calcium ion influx, stimulation of membrane phospholipid degradation and subsequent free-fatty-acid accumulation, and free radical generation.

Knowledge of these underlying events has led investigators studying certain types of ischemic injury to utilize agents such as calcium channel blockers, glutamate and glycine antagonists, CDP-amines, free radical scavengers/antioxidants, perfluorocarbons and thrombolytic agents to improve cerebral blood flow and/or neurological outcome, all with mixed results. Though calcium-channel blockers have been reported to decrease infarct size, these drugs also have been reported to produce inconsistent results and undesirable side effects, such as reduction in pulse or perfusion pressure [Kaste M et al. A Randomized, Double-blind, Placebo-Controlled Trial of Nimodipine in Acute Ischemic Hemispheric Stroke. *Stroke*. 1994; 25:1348–1353].

More particularly, glutamate antagonists have been observed to reduce infarct size under certain experimental conditions [Olney J. W. et al. NMDA Antagonist Neurotoxicity: Mechanism and Prevention. *Science*. 1991; 254:1515–1518]. However, most, if not all, of these compounds cause brain vacuolization and most produce phencyclidine-like subjective effects in animals and humans. Ingestion of phencyclidine, commonly known as PCP, has been associated with euphoria, anxiety, mood lability, and prolonged psychotic states.

Free radical scavengers/antioxidants are a heterogenous group of compounds. In general, the effects of these compounds on infarct volume have been inconsistent. For example, superoxide dismutase inhibitors have been found to reduce infarct volume only when injected intracerebroventricularly [Kinouchi H et al. Attenuation of focal cerebral ischemic injury in transgenic mice overexpressing CuZn superoxide dismutase. *Proc. Natl. Acad. Sci. USA*. 1991; 88:11158–11162]. Other compounds, such as lubeluzole, have been shown to have clinical benefit [Diener H. C. et al. The Effects of Lubelezole in the Acute Treatment of Ischemic Stroke: Results of a Phase 2 Trial. *Stroke*. 1995; 26:30], but with a very narrow margin of safety.

Although perfluorocarbons have shown some benefit in the outcome from ischemic stroke, these compounds have an extremely long half-life and must be infused into the brain and spinal fluid. In addition, these compounds have been observed to cause gonadal hypertrophy [Bell R. D. et al. A Novel Treatment for Ischemic Intracranial Hypertension in Cats. *Stroke*. 1991; 22:80–83].

Thrombolytic agents, such as t-PA (tissue plasminogen activator), streptokinase, and urokinase, have shown some promise in the treatment of ischemia. However, these agents have the propensity to increase intracranial bleeding, which, ultimately, can lead to increased mortality. [del Zoppo G. J. et al. Thrombolytic Intervention in Acute Thrombotic and Embolic Stroke. *Seminars in Neurology*. 1991; 11/4:368–384; The Ancrod Stroke Study Investigators. Ancrod for the Treatment of Acute Ischemic Brain Infarction. *Stroke*. 1994; 25:1755–1759; Hacke W et al. The efficacy of IV-tPA in acute ischemic stroke: First results of the ECASS trial. *Stroke*. 1995; 26:167].

SUMMARY OF THE INVENTION

The present invention relates to a method for reducing the extent of cerebral infarction subsequent to cerebral ischemia caused by any of a number of disorders, comprising administering an amount of citicoline (CDP-choline) or a pharmaceutically-acceptable salt thereof. Such disorders include thromboembolic or hemorrhagic stroke, cerebral vasospasm, hypoglycemia, cardiac arrest, and status epilepticus, and also may include schizophrenia, epilepsy, neurodegenerative disorders, Alzheimer's disease, and Huntington's disease.

The present invention also relates to a pharmaceutical composition for the prevention or reduction of cerebral infarction, comprising an amount of citicoline effective to prevent or reduce cerebral infarction and a pharmaceutically acceptable carrier.

Citicoline may be expected to have a number of advantages over other agents being developed for the reduction of infarct size subsequent to an ischemic event. Being an endogenous compound, citicoline is inherently safe. Citicoline has a very low toxicity and an extremely broad therapeutic index.

The potential mulitmodal action of citicoline also may prove advantageous. Although the relative contribution of each potential mechanism to the reduction of infarct size is unknown, citicoline and its hydrolysis products—cytidine and choline—are believed to play important roles in the generation of phospholipids involved in membrane formation and repair. These compounds also are believed to contribute to critical metabolic functions, such as the formation of nucleic acids and proteins, and the synthesis of the neurotransmitter acetylcholine [Ulus I. H. et al. Choline increases acetylcholine release and protects against the stimulation-induced decreased in phosphatide levels within membranes of rat corpus striatum. *Brain Research*. 1989; 484:217–227]. Thus, under ischemic conditions, citicoline may function to (1) stabilize membranes by providing substrate for membrane maintenance; (2) repair damaged membranes by supplying important substrates for membrane formation; and (3) restore neuronal function by supplying substrate for the formation of acetylcholine. Moreover, unlike other, proposed therapeutic agents, citicoline has the potential not only to reduce initial infarct size, but also to contribute to the repair of the damaged area.

DETAILED DESCRIPTION

Figure 1:
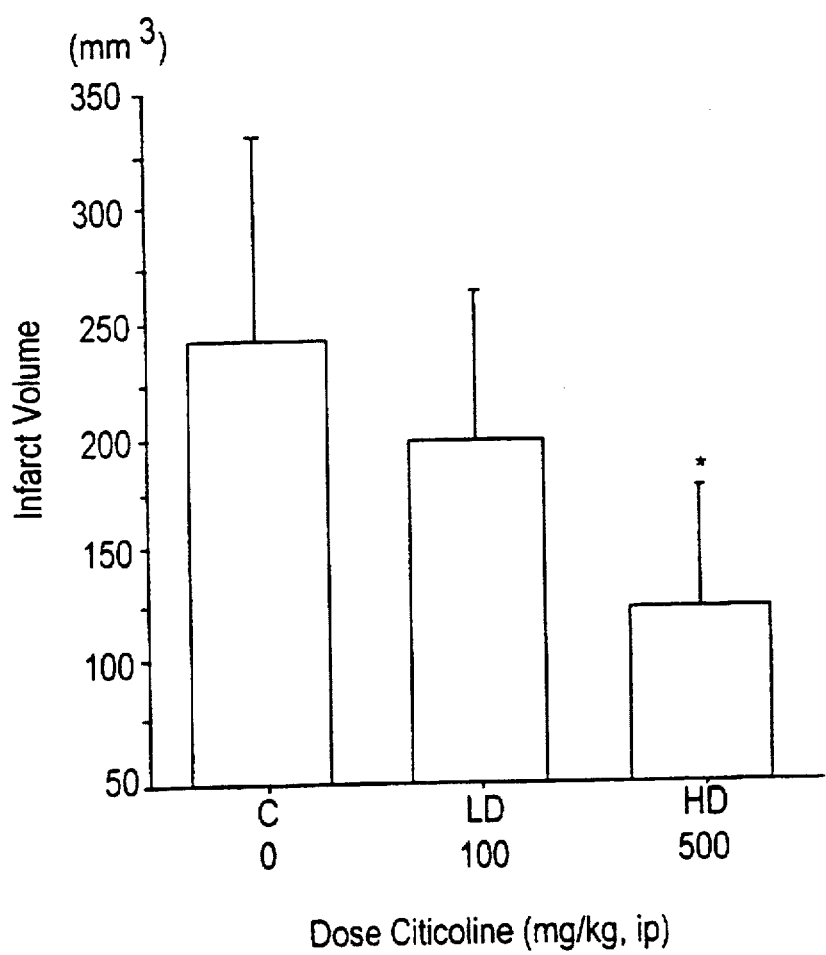
FIG. 1 depicts bar graphs of infarct volume in animal groups receiving vehicle control, 100 mg/kg citicoline, and 500 mg/kg citicoline. Values are mean±standard deviation (SD).

In the brain, citicoline, a naturally occurring endogenous nucleoside, is the rate limiting factor for the formation of phosphatidylcholine, an essential phospholipid for maintenance of intracellular and extracellular membrane structures. Ischemia-induced high energy failure leads, through ATP depletion, to phosphatidylcholine degradation and free fatty acid accumulation. Release of the unsaturated free fatty acid arachidonic acid has been observed to induce brain edema during cerebral infarction. In addition, free fatty acids have been observed, in vitro, to inhibit oxidative phosphorylation in mitochondria. Previous investigators have reported that exogenous citicoline administration can stimulate phosphatidylcholine synthesis and prevent free fatty acid release. Others investigating the phenomenon of focal and global ischemia have noted a decreased mortality and improved neurological function in citicoline-treated animals.

The present invention is directed to a new and important use of citicoline—the reduction of infarct size subsequent to cerebral ischemia. Although stabilization of membranes is believed to be of benefit in ischemic conditions, it has not been definitively demonstrated that membrane stabilization will lead to reduced infarct volume. The administration of citicoline has been shown to produce rapid, acute increases in acetylcholine release. In addition, the administration of citicoline to normal, healthy rats, over a ninety (90) day period has been observed to lead to increased brain phosphatidylcholine synthesis, and, hence, increased membrane formation. The present inventors, on the other hand, have unexpectedly found that administration of citicoline for just seven (7) days, significantly reduces infarct volume, presumably by altering phosphatidylcholine synthesis and membrane formation.

The cerebroprotective action of citicoline was demonstrated in a model of temporary forebrain ischemia in the rat in which the middle cerebral artery (MCA) is occluded by suture. Treatment with 500 mg/kg of citicoline significantly reduced the mean volume of infarction compared with controls.

For medical use, the amount required of citicoline, or a pharmacologically-acceptable salt thereof ("the active ingredient") to achieve a therapeutic effect, will vary with the route of administration and the particular disorder or disease to be treated. A suitable systemic dose of the active ingredient, for a mammal suffering from, or likely to suffer from, any of the conditions described herein, is in the range of 100 mg to 4000 mg per day, with a preferred dose of 1000 mg per day, administered 500 mg b.i.d. The preferred dose of 1000 mg citicoline per day will produce a plasma choline concentration of 1.5 ng/ml, the same as that produced by the administration of 500 mg/kg/day citicoline to the rat, as further described in the Example.

While it is possible for the active ingredient to be administered alone, it may be preferable to present the active ingredient as a formulation.

Formulations of the active ingredient, suitable for oral administration, may be in the form of discrete units, such as capsules, cachets, tablets, or lozenges; in the form of a powder or granules for reconstitution; in the form of a solution or a suspension in an aqueous liquid or nonaqueous liquid; or, in the form of an oil-in-water emulsion or a water-in-oil emulsion. The active ingredient also may be in the form of a bolus, electuary, or paste.

Formulations of the active ingredient, suitable for parenteral administration, may comprise a sterile, aqueous preparation of the active ingredient.

In addition to containing the standard and well-known pharmaceutical carriers and/or excipients, all of the above formulations may contain other therapeutically-active substances. The formulations may be presented in unit dosage form and may be prepared by any of the methods well-known in the art of pharmacy.

The present invention is illustrated by the example which follows; it being understood, however, that the invention is not limited to the specific details of this example.

EXAMPLE

Thirty male, Sprague-Dawley rats, weighing 280–350 grams, randomly were divided into three groups of ten rats each: ten animals to be treated with 500 mg/kg citicoline; ten animals to be treated with 100 mg/kg citicoline; and ten control animals to be treated with physiological saline, the vehicle for citicoline.

All animals were anesthetized with 400 mg/kg chloral hydrate administered intraperitoneally. The left femoral artery was cannulated with PE-50 polyethylene tubing for continuous monitoring of arterial blood pressure and blood sampling for analysis of arterial blood gases.

Measurements were recorded prior to surgery, one hour after ischemia, and two hours after ischemia, before reperfusion. Rectal temperature was maintained at 37° C. with a thermostatically-controlled heating lamp during the surgery and MCA occlusion.

The right MCA was occluded through a transvascular approach as previously described. [Minematsu K et al. Diffusion weighted magnetic resonance imaging: Rapid and quantitative detection of focal brain ischemia. *Neurology* 1992; 42: 235–240; Zea Longa E et al. Reversible middle cerebral artery occlusion. *Stroke* 1989; 20: 84–91]. Briefly, the right common carotid artery (CCA) and the right external carotid artery were exposed through a midline neck incision. The distal CCA and the external carotid artery were ligated with a 3-0 silk suture. A 4-0 monofilament nylon suture (40 mm length), whose tip had been rounded by heating near a flame and then coated with silicon (Bayer, Leverkusen, Germany), was inserted through an arteriectomy of the CCA and gently advanced into the internal carotid artery. When positioned approximately 17 mm from the carotid bifurcation, the tip of the suture occludes unilaterally the proximal anterior cerebral artery, the origins of the MCA and the posterior communicating artery. To prevent bleeding, the CCA was loosely ligated, just distal to the arteriotomy, with a 3-0 silk suture.

After 110 minutes of ischemia, the animals were treated with 500 mg/kg citicoline; with 100 mg/kg citicoline; or with 0.3 ml physiologic saline vehicle (controls), administered intraperitoneally. The MCA occluder and femoral artery catheter then were removed, after a total ischemic period of two (2) hours, permitting reperfusion of the tissue. The animals were allowed to recover from the anesthesia and to eat and drink freely. This procedure was repeated for 6 additional days. On the seventh day of treatment, the animals were reanesthetized with 400 mg/kg chloral hydrate administered intraperitoneally and then decapitated.

The brains were quickly removed, inspected to confirm that no subarachnoid hemorrhage had occurred, and coronally sectioned into six, 2 mm slices. The brain slices were incubated for 30 minutes in a 2% solution of 2,3,5-triphenyltetrazolium chloride (TTC) at 37° C. and fixed by immersion in a 10% buffered formalin solution. TTC stains normal brain tissue (intact cellular membrane) red; ischemic tissue, pink; and necrotic tissue, white. Six brain sections per animal were TTC-stained and photographed using a charge couple device camera (EDC-1000HR Computer Camera, Electrim Corporation, Princeton, N. J.), with the images stored on a microcomputer.

As brain edema is known to affect the measurement of infarct size, an image processing software package (Bio Scan OPTIMAS, Edmonds, Wash.) was utilized to calculate a corrected infarct volume. Corrected infarct area was calculated using the equation: corrected infarct area equals left hemisphere area minus (right hemisphere area minus infarct area). Corrected infarct volume was calculated by multiplying the corrected infarct area by slice thickness.

Five of ten animals in the control group died between 24 and 48 hours after MCA occlusion. Five of ten animals in the 100 mg/kg group died; four between 24 and 48 hours and one on the fifth day. Three of ten animals in the 500 mg/kg group died; two between 24 and 48 hours and one on the sixth day.

As depicted in FIG. 1, the mean volume of infarction in the control group was 243.5±88.6 mm$^3$ (mean±SD); in the 100 mg/kg group, 200.2±19.9 mm$^3$; in the 500 mg/kg group, 125.5±45.2 mm$^3$. The difference of the mean values of infarct volume was significant for the control versus 500 mg/kg group ($p<0.01$, Scheffe's test). Though there was no significant difference between the control and 100 mg/kg group, there was a trend towards smaller infarction volume in the 100 mg/kg group.

What is claimed is:

1. A method of protecting brain tissue from cerebral infarction subsequent to ischemia comprising administering an effective amount of citicoline, excluding effective amounts of cytidine diphosphoethanolamine, cytidine diphospho-N-methylethanolamine, cytidine diphospho-N, N-dimethylethanolamine, or mixtures thereof, to a subject in need thereof such that the extent of cerebral infarction subsequent to ischemia is reduced compared to the extent of cerebral infarction in control subjects.

2. The method of claim 1 in which said effective amount of citicoline ranges from 100 mg to 4000 mg per day administered orally.

3. The method of claim 1 in which 500 mg per day of citicoline is administered.

4. The method of claim 1 in which 500 mg of citicoline is administered twice daily.

5. The method of claim 1 in which the cerebral infarction is caused by a stroke.

6. The method of claim 2 in which 1000 mg per day of citicoline is administered.

7. The method of claim 1 in which said citicoline is administered in the form of a capsule, cachet, tablet, or lozenge.

8. The method of claim 1 in which said citicoline is administered in the form of a powder or granule for reconstitution.

9. The method of claim 1 in which said citicoline is administered in the form of a solution or a suspension in an aqueous liquid or nonaqueous liquid.

10. The method of claim 1 in which said citicoline is administered in the form of an oil-in-water emulsion or a water-in-oil emulsion.

11. The method of claim 1 in which said citicoline is administered in the form of a bolus, electuary, or paste.

* * * * *

UNITED STATES PATENT AND TRADEMARK OFFICE
CERTIFICATE OF CORRECTION

PATENT NO.     : 5,801,160
DATED          : September 1, 1998
INVENTOR(S)    : Bobby Winston Sandage et al.

It is certified that error appears in the above-identified patent and that said Letters Patent is hereby corrected as shown below:

<u>Title page,</u>
The *Attorney, Agent, or Firm* should read -- Gilberto M. Villacorta, Pepper Hamilton LLP --.

Signed and Sealed this

Tenth Day of December, 2002

JAMES E. ROGAN
*Director of the United States Patent and Trademark Office*